(12) United States Patent
Sykes

(10) Patent No.: US 11,890,207 B2
(45) Date of Patent: Feb. 6, 2024

(54) RELEASE MECHANISM

(71) Applicant: Hugh Steeper Limited, Leeds (GB)

(72) Inventor: James Sykes, Leeds (GB)

(73) Assignee: Hugh Steeper Limited, Leeds (GB)

( * ) Notice: Subject to any disclaimer, the term of this patent is extended or adjusted under 35 U.S.C. 154(b) by 105 days.

(21) Appl. No.: 17/691,795

(22) Filed: Mar. 10, 2022

(65) Prior Publication Data

US 2022/0287855 A1    Sep. 15, 2022

(30) Foreign Application Priority Data

Mar. 10, 2021  (GB) ..................... 2103285

(51) Int. Cl.
*A61F 2/58* (2006.01)
*A61F 2/68* (2006.01)
*A61F 2/70* (2006.01)

(52) U.S. Cl.
CPC ............... *A61F 2/68* (2013.01); *A61F 2/586* (2013.01); *A61F 2002/6836* (2013.01); *A61F 2002/6854* (2013.01); *A61F 2002/701* (2013.01)

(58) Field of Classification Search
CPC .... A61F 2/68; A61F 2/586; A61F 2002/6836; A61F 2002/6854; A61F 2002/701
See application file for complete search history.

(56) References Cited

U.S. PATENT DOCUMENTS

| | | | | |
|---|---|---|---|---|
| 5,195,807 A | * | 3/1993 | Lederman | F16C 33/726 |
| | | | | 301/108.3 |
| 7,654,546 B2 | * | 2/2010 | Watarai | B62K 25/02 |
| | | | | 280/288.4 |
| 11,617,666 B2 | * | 4/2023 | Hendriks | A61F 2/6607 |
| | | | | 623/55 |
| 2018/0256366 A1 | | 9/2018 | Bai | |
| 2022/0346985 A1 | * | 11/2022 | Pulver | A61F 2/80 |

FOREIGN PATENT DOCUMENTS

GB        252545 A       6/1926
WO   2019215578 A1    11/2019

OTHER PUBLICATIONS

Sykes, J., GB2103285.9, United Kingdom Intellectual Property Search Report, dated Jul. 23, 2021, 1 page.

* cited by examiner

*Primary Examiner* — Bruce E Snow
(74) *Attorney, Agent, or Firm* — Rahman LLC

(57) ABSTRACT

A release mechanism especially but not exclusively for use in a prosthetic hand. The release mechanism includes a retainer and a release pin held within the retainer so as to be moveable between an engagement position and a release position. The retainer is provided with portions which engage the release pin to restrain it to movement between the engagement position and the release position. The portions include ball bearings to reduce the friction between the retainer and the release pin. Also, a prosthetic hand having such a release mechanism is provided so that the user can release the hand if it becomes jammed.

15 Claims, 4 Drawing Sheets

RELEASE MECHANISM

CROSS-REFERENCE TO RELATED APPLICATION

This application claims priority to United Kingdom Patent Application No. 2103285.9 filed on Mar. 10, 2021 and entitled "A Release Mechanism", the complete disclosure of which, in its entirety, is herein incorporated by reference.

The present invention relates to a release mechanism especially but not exclusively for use in a prosthetic hand, comprising a retainer and a release pin held within the retainer so as to be moveable between an engagement position and a release position, the retainer being provided with portions which engage the release pin to restrain it to movement between the said engagement position and the said release position.

Such a release mechanism may be a safety release mechanism for a prosthetic hand in which there are at least two digits which are moveable towards and away from one another by means of a motor drive, the motor drive being coupled to at least one of those digits via a drive engagement part of the release pin when the latter is in its engagement position but is de-coupled from the motor drive when the release pin is in its release position, whereby in the event that the said at least two digits are jammed in position relative to one another, the release pin can be moved to its release position to enable the digit to which the motor drive is coupled to be freed from its jammed position. In this way the user can manually override the drive system and open the prosthetic hand in an emergency.

A disadvantage of such a release mechanism as constructed hitherto is that in the event of such jamming, frictional forces acting between the retainer and the release pin inhibit movement of the pin out of its engagement position, possibly to the extent that the user is unable to operate the safety release mechanism, which in turn may result in injury to the user. At the very best, with such a prosthetic hand safety release mechanism it might be difficult for the user to activate the override of the mechanism and disengage for example a gripping action of the prosthetic hand owing to the frictional force between the retainer and the release pin.

The present invention seeks to provide a remedy.

Accordingly, the present invention is directed to a release mechanism having the construction set out in the opening paragraph of the present specification, in which the said portions comprise rolling-element bearings which are free to rotate to facilitate movement of the release pin between its engagement position and its release position.

This provides the advantage of reduced frictional forces between the release pin and the retainer, to ease movement of the release pin to its release position freeing the digit to which the motor drive is coupled and hence release the gripping action or other action of the prosthetic hand which caused it to jam, for example by rotation of that digit.

The frictional forces may be further reduced if the rolling-element bearings comprise ball bearings.

The roller members may be provided in a cage surrounding the release pin.

This further reduces the unwanted friction between the pin and the retainer.

The present invention extends to such a prosthetic hand having such a release mechanism.

An example of a release mechanism made in accordance with the present invention and a prosthetic hand made in accordance with the present invention will now be described in greater detail with reference to the accompanying drawings, in which.

Figure 1:
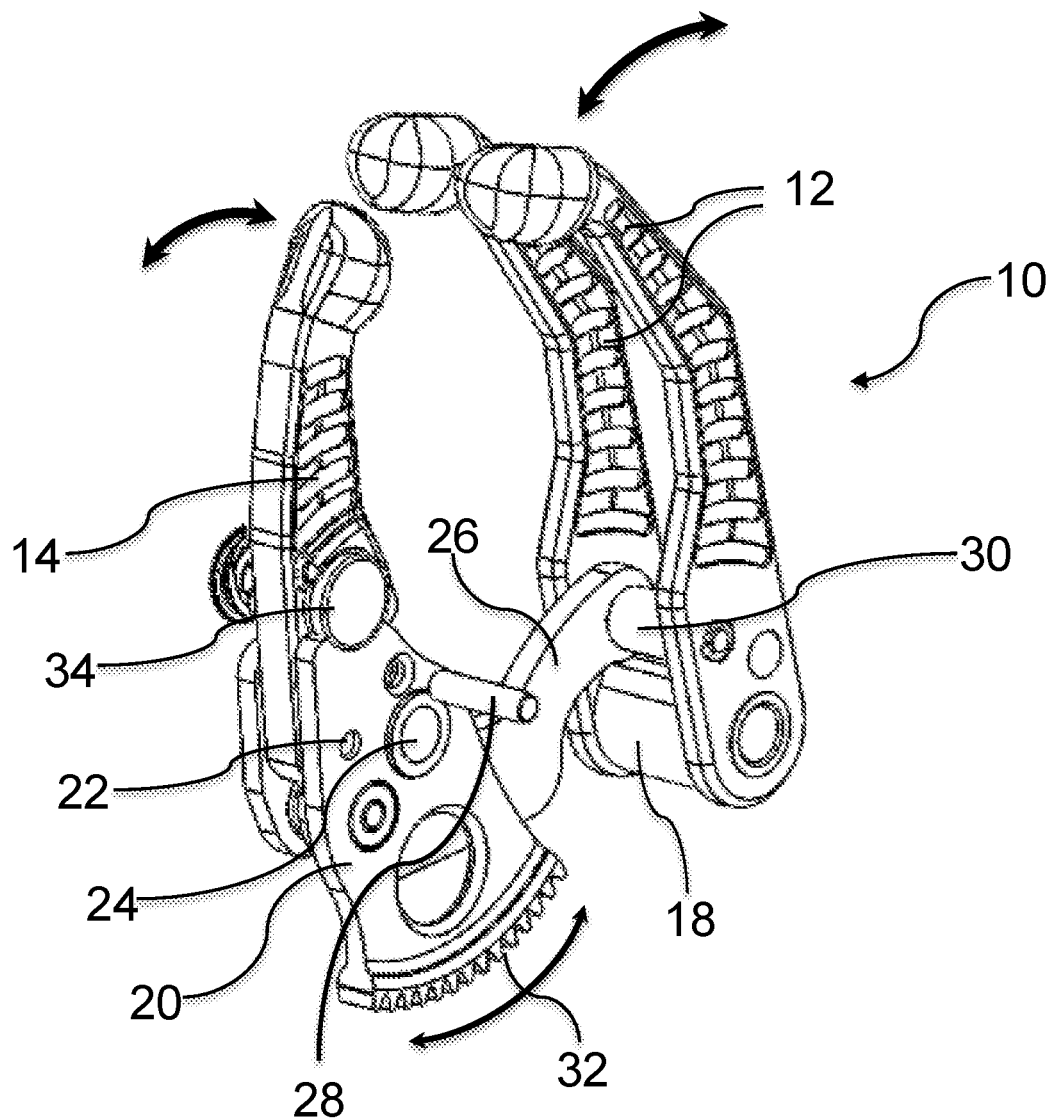
FIG. 1 is a perspective view of parts of a prosthetic hand embodying the present invention with a release mechanism embodying the present invention.
Figure 2:
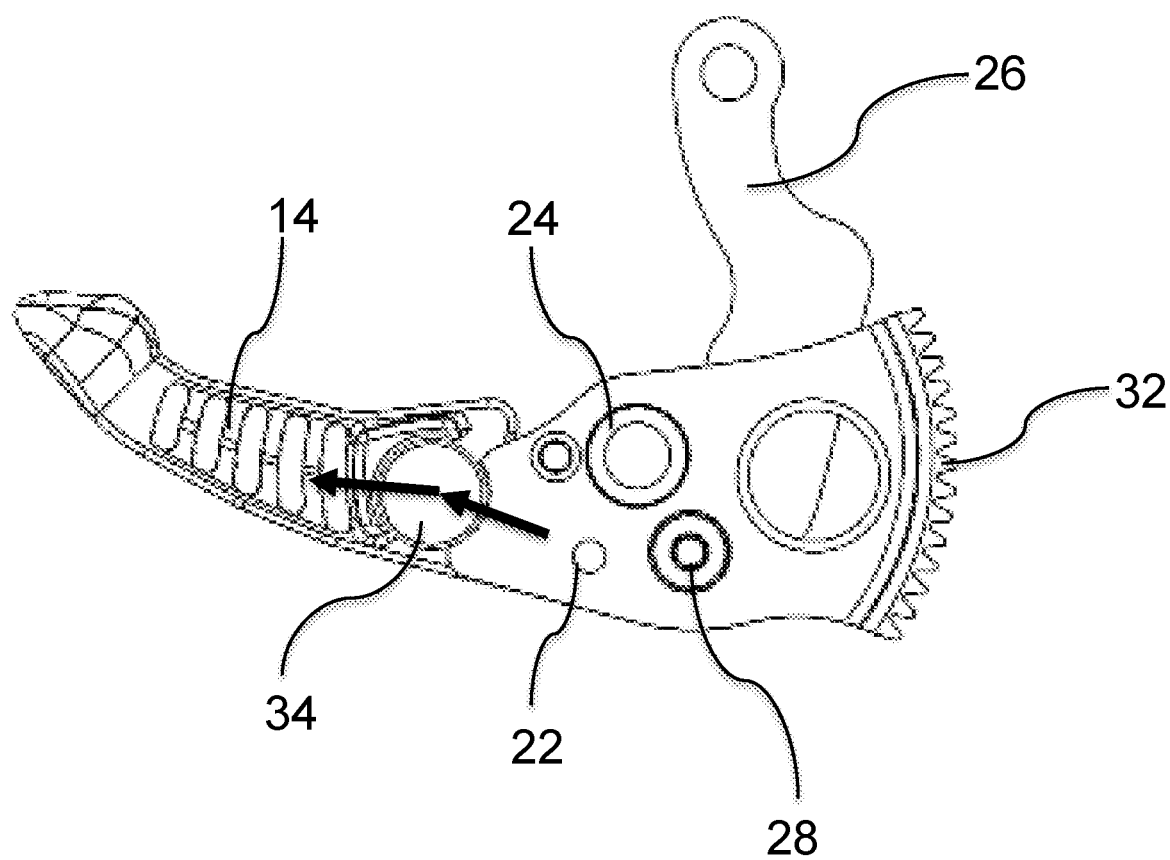
FIG. 2 is an explanatory side view of parts of the hand shown in FIG. 1 in an engaged position.

A myoelectric prosthetic hand 10, parts of which are shown in FIGS. 1 to 5, comprises two digits 12 in the form of fingers fixed in registration with one another, with a further distal or digit 14 corresponding to the thumb of a hand. A cylindrical sleeve 18 is provided fixed to the bases of the digits 12. A pivot shaft (not shown) of the prosthetic hand 10 extends through the sleeve 18 enabling the digits 12 to rotate about the axis of that pivot shaft.

The base of the digit 14 is attached to a gear 20 by a pivot pin 22. The gear 20 is provided with a sleeve 24 through which a further pivot shaft (not shown) of the prosthetic hand 10 extends, the first mentioned pivot shaft and the further pivot shaft being fixed relative to one another. The gear 20 and with it the digit 14 can rotate about the said further pivot shaft.

The gear 20 and the digits 12 are coupled to one another by a lever 26 which can pivot about pins 28 and 30 of the gear 20 and the digits 12 respectively.

The gear 20 is formed with a series of teeth 32 on an arcuate lower edge of the gear 20 the centre of which lies on the axis of the pivot shaft (not shown) which extends through the sleeve 24 of the gear 20.

Figure 4:
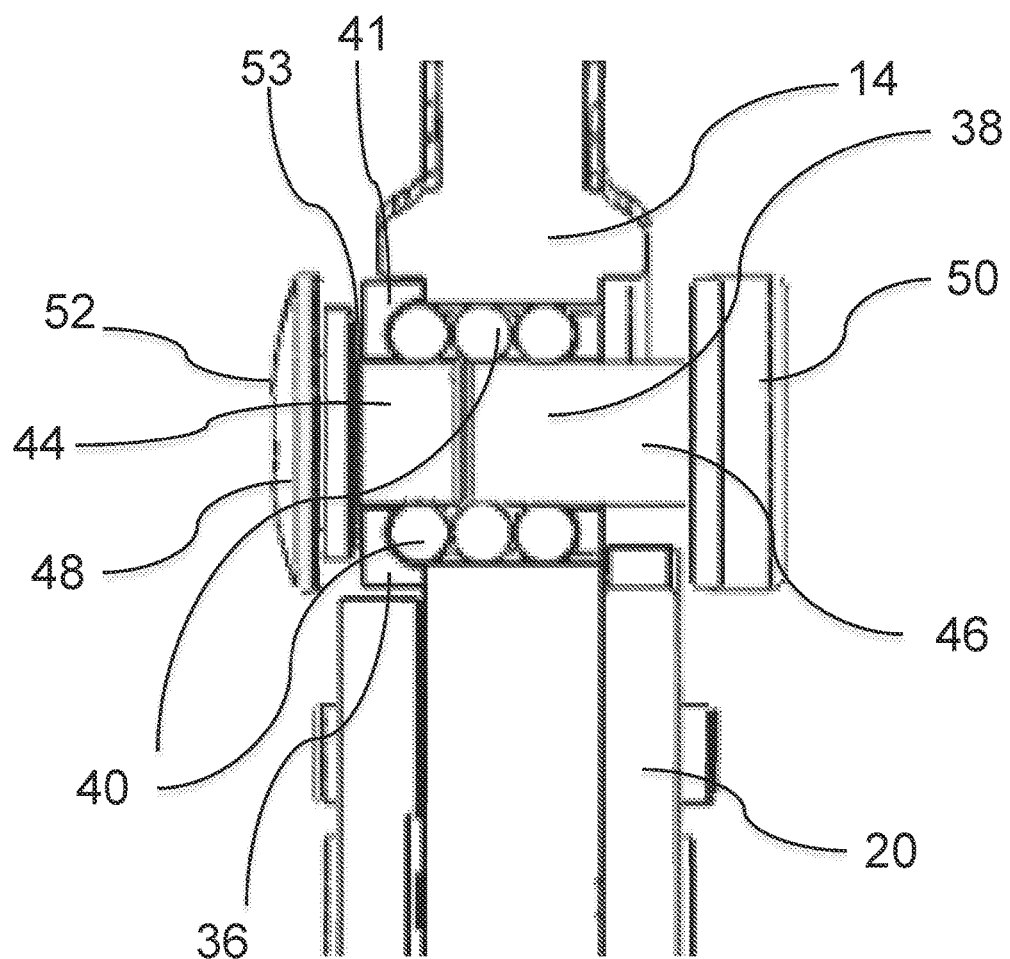
FIG. 4 shows a cross-section of the release mechanism shown in FIG. 1.
Figure 5:
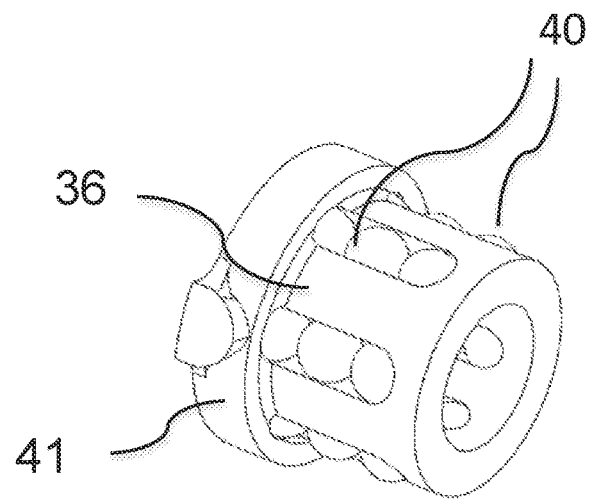
FIG. 5 is a perspective view of a retainer of the release mechanism shown in FIG. 4.

Rotation of the digit 14 about the pivot pin 22 is normally prevented by a safety release mechanism 34 of the prosthetic hand 10 shown more clearly in FIG. 4. This comprises a linear bearing 36. The linear bearing 36 is in the form of a hollow cylindrical retainer 36 which extends through a base of the digit 14 and is spaced from the pivot pin 22. A cylindrical release pin 38 is coaxial with and extends through the retainer 36. The retainer 36 is in the form of a cage housing six rows each of three ball bearings 40, the rows extending longitudinally of the axis of the retainer 36 and being uniformly spaced around that axis. The ends of the rows are co-planar with one another. Thus respective ends of the rows lie on an inner face of a flange 41 of the retainer 36. The rows are also parallel to one another. Thus the retainer 36 holds three rings of ball bearings 40 each of six ball bearings. Each ring surrounds the release pin 38 of the release mechanism 34. At least some of the ball bearings are in contact with the release pin 38 at any one time.

The release pin 38 is formed of two parts 44 and 46 which are in screw threaded engagement with one another, the screw threaded engagement being coaxial with the release pin 38 as a whole. Both the outer ends of these parts 44 and 46 are provided with discs or circular heads 48 and 50 respectively, both of which having a larger diameter than a cross section through the release pin 38 which is uniform along its length between the heads 48 and 50. The circular head 48 has a rounded outer surface 52. A compression spring 53 extends between the circular head 48 and an outer face of the flange 41. The circular head 50 of the release pin 38 engages an arcuate recess 54 in an end of the gear 20 remote from the teeth 32 and on the opposite side of the sleeve 24. This fixes the digit 14 relative to the gear 20.

When in use, a motor drive (not shown) coupled to the teeth 32 via a gearbox (not shown) is operated to apply a torque to rotate the gear 20 about the pivot shaft (not shown) that extends within the sleeve 24. This drive force is transmitted to the digit 14 via the head 50 as indicated by the arrows in FIG. 2 so that the digit 14 rotates with the gear 20. At the same time the drive force is transmitted through the lever 26 to rotate the digits 12 in the opposite sense to the digit 14, in the manner indicated by the arcuate arrows in FIG. 1, so that the digits 12 and the digit 14 either move towards one another, in a gripping action, or away from one another to open the prosthetic hand.

Figure 3:
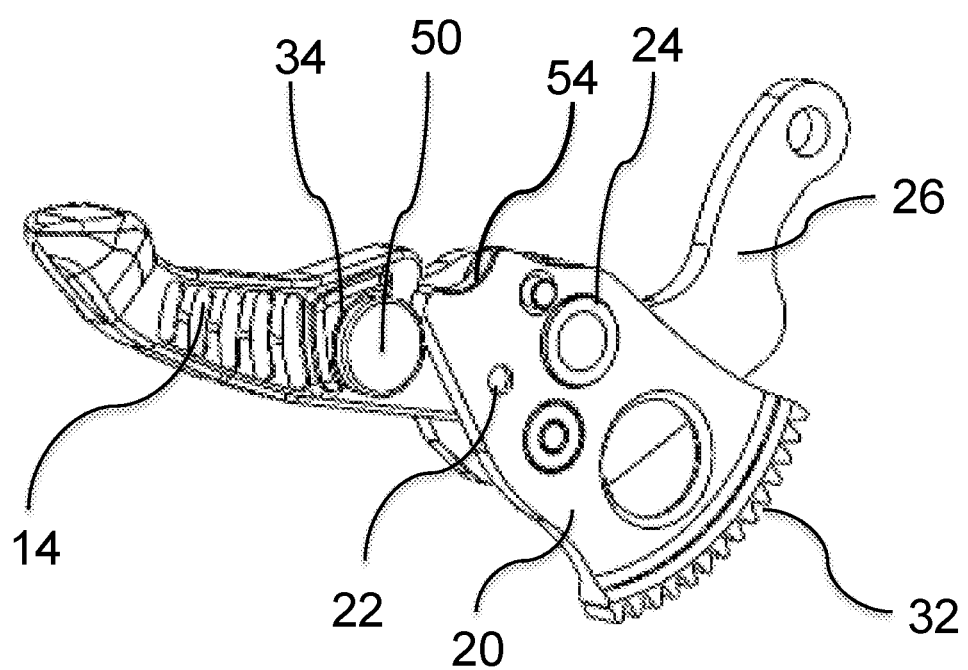
FIG. 3 is a perspective view of the parts shown in a disengaged position.

In the event that the prosthetic hand jams whilst applying a gripping action on an object to be grasped, the release pin 38 may be subject to forces as great as 400 N. In this situation, because the ball bearings 40 reduce the frictional forces which act on the release pin 38, and notwithstanding the forces to which the release pin 38 is subjected, the user may manually override the drive torque to release the grip. Thus the user may move the release pin 38 from the engagement position it has shown in FIGS. 1 and 2 manually by pushing in the head 48 towards the base of the digit 14 against the force of the compression spring 53 so that the release pin is shifted longitudinally to its release position shown in FIGS. 3 and 4, in which the head 50 is disengaged from the gear 20 and the digit 14 can be rotated away from the digits 12 about the pivot pin 22, as shown in FIG. 3.

To re-engage the digit 14, the latter may be rotated until the head 50 is back in registration with the recess 54 of the gear 20, whereupon the head 50 re-engages the gear 20 by virtue of the spring biasing provided by the compression spring 53. The spring biasing also inhibits rolling out of the retainer 36 from the digit 14 upon such re-engagement. As a result this can be achieved without further resetting the prosthetic hand by a specialist.

Numerous variations and modifications to the illustrated embodiment of the present invention may occur to the reader without taking the resulting constructions outside the scope of the accompanying claims. For example the ball bearings 40 may be fewer in number, or greater in number. They may be retained in two or more ring cages. Such ring cages may be spaced apart along the axis of the retainer 36.

What is claimed is:

1. A release mechanism for use in a prosthetic hand, the release mechanism comprising:
   a retainer; and
   a release pin held within the retainer so as to be moveable between an engagement position and a release position, wherein the release pin comprises:
      a first part comprising a first longitudinal body;
      a second part comprising a second longitudinal body, wherein the first part is connected to the second part such that the first longitudinal body and the second longitudinal body form an elongated body having a uniform diameter; and
      a disc head positioned at each end of the first part and the second part, wherein the disc head is configured to engage a recess of a gear,
   wherein the retainer being provided with portions which engage the release pin to restrain the release pin to movement between the engagement position and the release position, in which the portions comprise rolling-element bearings which are free to rotate to facilitate movement of the release pin between the engagement position and the release position.

2. A release mechanism according to claim 1, in which the rolling-element bearings comprise ball bearings.

3. A release mechanism according to claim 1, in which the rolling-element bearings are provided in a cage surrounding the release pin.

4. A release mechanism according to claim 3, in which the release pin is spring-biased towards the engagement position.

5. A release mechanism according to claim 1, in which the release pin is spring-biased towards the engagement position.

6. A release mechanism according to claim 2, in which the rolling-element bearings are provided in a cage surrounding the release pin.

7. A release mechanism according to claim 2, in which the release pin is spring-biased towards the engagement position.

8. A prosthetic hand comprising:
   a release mechanism comprising:
      a retainer; and
      a release pin held within the retainer so as to be moveable between an engagement position and a release position, wherein the release pin comprises:
         a first part comprising a first longitudinal body;
         a second part comprising a second longitudinal body, wherein the first part is connected to the second part such that the first longitudinal body and the second longitudinal body form an elongated body having a uniform diameter; and
         a disc head positioned at each end of the first part and the second part, wherein the disc head is configured to engage a recess of a gear,
      wherein the retainer being provided with portions which engage the release pin to restrain the release pin to movement between the engagement position and the release position, in which the portions comprise rolling-element bearings which are free to rotate to facilitate movement of the release pin between the engagement position and the release position.

9. A prosthetic hand according to claim 8, in which there are at least two digits which are moveable towards and away from one another by means of a motor drive, the motor drive being coupled to at least one of those digits via a drive engagement part of the release pin when the latter is in its engagement position but is de-coupled from the motor drive when the release pin is in its release position, whereby in the event that the said at least two digits are jammed in position relative to one another, the release pin can be moved to its release position to enable the digit to which the motor drive is coupled to be freed from its jammed position.

10. A prosthetic hand according to claim 8, in which the rolling-element bearings comprise ball bearings.

11. A prosthetic hand according to claim 10, in which the rolling-element bearings are provided in a cage surrounding the release pin.

12. A prosthetic hand according to claim 11, in which the release pin is spring-biased towards the engagement position.

13. A prosthetic hand according to claim 10, in which the release pin is spring-biased towards the engagement position.

14. A prosthetic hand according to claim 8, in which the rolling-element bearings are provided in a cage surrounding the release pin.

15. A prosthetic hand according to claim 8, in which the release pin is spring-biased towards the engagement position.

\* \* \* \* \*